US010231821B2

(12) United States Patent
Gabriele et al.

(10) Patent No.: US 10,231,821 B2
(45) Date of Patent: Mar. 19, 2019

(54) COMPOSITE LUMEN WITH REINFORCING TEXTILE AND MATRIX (71) Applicant: SECANT MEDICAL, INC., Perkasie, PA (US)

(72) Inventors: Peter D Gabriele, Perkasie, PA (US); Sean Christopher Gasby, Perkasie, PA (US); Jeremy J. Harris, Doylestown, PA (US); Alicia Ruthrauff, Bethlehem, PA (US); Swati Amin, Delran, NJ (US); Seth A. Winner, Glenside, PA (US); Ryan Heniford, Schwenksville, PA (US); Richard Balthaser, Bethel, PA (US); Emily Y. Ho, Wayne, PA (US)

(73) Assignee: THE SECANT GROUP, LLC, Telford, PA (US)

(*) Notice: Subject to any disclaimer, the term of this patent is extended or adjusted under 35 U.S.C. 154(b) by 0 days.

(21) Appl. No.: 14/707,588

(22) Filed: May 8, 2015

(65) Prior Publication Data
US 2015/0320542 A1 Nov. 12, 2015

Related U.S. Application Data (60) Provisional application No. 61/990,295, filed on May 8, 2014.

(51) Int. Cl.
A61F 2/06 (2013.01)
A61F 2/07 (2013.01)
(Continued)

(52) U.S. Cl.
CPC ............ A61F 2/07 (2013.01); A61F 2/04 (2013.01); A61F 2/86 (2013.01); A61F 2/88 (2013.01);
(Continued)

(58) Field of Classification Search
CPC ............ A61F 2210/0004; A61F 2/82; A61F 13/00068; A61F 2002/823;
(Continued)

(56) References Cited

U.S. PATENT DOCUMENTS 5,800,512 A   9/1998  Lentz et al.
6,017,566 A   1/2000  Bunczek et al.
(Continued)

FOREIGN PATENT DOCUMENTS

JP   H06-7387 A    1/1994
JP   H11-504548 A  4/1999
(Continued)

OTHER PUBLICATIONS

R. Allen, et al., Nerve regeneration and elastin formation within poly(glycerolsebacate)-based synthetic arterial grafts one-year post-implantation in a rat model,Biomaterials, vol. 35, No. 1, p. 166 and 172, 2013.
(Continued)

Primary Examiner — Ann Schillinger
(74) Attorney, Agent, or Firm — McNees Wallace & Nurick LLC (57) ABSTRACT A composite hollow lumen and a method for producing the lumen are provided. The lumen includes a tubular textile formed of yarns having a first tensile strength and a matrix material in which the tubular textile is embedded to form a conduit having a bore and a sidewall substantially impermeable to liquid. The matrix material has a second tensile strength that is lower than the first tensile strength. The method for producing a composite lumen includes selecting yarns having a first tensile strength, selecting an elastomeric matrix material having a second tensile strength that is lower that the first tensile strength, forming a tubular textile of the yarns, and embedding the tubular textile in the matrix
(Continued)

material to form a conduit having a bore and conduit walls that are substantially impermeable to liquid. The elastomeric matrix material is a biodegradable or bioresorbable polyester.

19 Claims, 7 Drawing Sheets (51) Int. Cl.
| | |
|---|---|
| *A61F 2/04* | (2013.01) |
| *A61F 2/86* | (2013.01) |
| *A61F 2/88* | (2006.01) |
| *A61L 31/06* | (2006.01) |
| *A61L 31/12* | (2006.01) |

(52) U.S. Cl.
CPC .............. *A61L 31/06* (2013.01); *A61L 31/12* (2013.01); *A61F 2002/072* (2013.01); *A61F 2210/0004* (2013.01)

(58) Field of Classification Search
CPC ...... A61F 2002/9511; A61F 2230/0069; A61F 2/0063; A61F 2/04; A61F 2/07; A61F 2/2487
See application file for complete search history.

(56) References Cited

U.S. PATENT DOCUMENTS

| | | | | |
|---|---|---|---|---|
| 6,217,609 | B1* | 4/2001 | Haverkost | A61F 2/90 623/1.13 |
| 6,444,782 | B1 | 9/2002 | Hamlin | |
| 7,722,894 | B2 | 5/2010 | Wang et al. | |
| 8,716,410 | B2 | 5/2014 | Venkatraman et al. | |
| 2002/0087176 | A1* | 7/2002 | Greenhalgh | A61F 2/064 606/155 |
| 2004/0039440 | A1* | 2/2004 | Elmaleh | A61F 2/07 623/1.42 |
| 2005/0133046 | A1* | 6/2005 | Becker | A61B 17/12109 128/898 |
| 2005/0169958 | A1* | 8/2005 | Hunter | A61B 17/11 424/423 |
| 2005/0228480 | A1 | 10/2005 | Douglas et al. | |
| 2006/0009839 | A1 | 1/2006 | Tan | |
| 2007/0023974 | A1* | 2/2007 | Wu | B29C 59/00 264/491 |
| 2007/0055299 | A1 | 3/2007 | Ishimaru et al. | |
| 2009/0082840 | A1* | 3/2009 | Rusk | A61F 2/95 623/1.11 |
| 2009/0214373 | A1 | 8/2009 | Stinson et al. | |
| 2010/0094404 | A1* | 4/2010 | Greenhalgh | A61B 19/026 623/1.15 |
| 2016/0242895 | A1 | 8/2016 | Matheny | |

FOREIGN PATENT DOCUMENTS

| | | |
|---|---|---|
| JP | 2001-333987 A | 12/2001 |
| JP | 2002-543950 A | 12/2002 |
| JP | 2004-208908 A | 7/2004 |
| JP | 2007-307132 A | 11/2007 |
| JP | 2007-536951 A | 12/2007 |
| JP | 2008-253297 A | 10/2008 |
| WO | 00/70018 A2 | 11/2000 |
| WO | 2013/154612 A2 | 10/2013 |

OTHER PUBLICATIONS

Sun, ZJ et. al., Materials Science and Engineering, The influence of lactic acid on the properties of Poly (glycerol-sebacate-lactic acid),2009, p. 178-182, C29.
Wang, Yadong et. al. A Tough Biodegradable Elastomer,vol. 20, p. 602-606, Jun. 2002, Nature Publishing Group.
Gao, Jin et. al., Macroporous Elastomeric Scaffolds with Extensive Micropores for Soft Tissue Engineering, Wallace H. Coulter Department of Biomedical Engineering, Georgia Institute of Technology,vol. 12, p. 917-925, Feb. 4, 2010, Mary Ann Liebert, Inc.
Jaafar, Israd et. al., Spectroscopic evaluation, thermal, and thermomechanical characterization of poly(glycerol-sebacate) with variations in curing temperatures and durations, J. Mater Sci, p. 2525-2529, Sep. 13, 2009, Springer Science+Business Media, LLC.
Pryor, Howard et. al., Poly(glycerol sebacate) films prevent postoperative adhesions and allow laparoscopic placement,Surgery, vol. 146, No. 3, p. 490-497, 2009, Boston, MA.
Guo, Xiao-Long et. al., Characterization and optimization of glycerol/sebacate ratio in poly(glycerol-sebacate elastomer for cell culture application, J. Biomed Mater Res Part A, vol. 102A, Issue 11, p. 3903-3907, Nov. 2014, Society for Biomaterials.
Chen, Qi-Zhi et. al., Characterisation of a soft elastomer poly(glycerol sebacate) designed to match the mechanical properties of myocardial tissue, ScienceDirect, p. 47-57, 2008, Biomaterials.

\* cited by examiner

COMPOSITE LUMEN WITH REINFORCING TEXTILE AND MATRIX

CROSS-REFERENCE TO RELATED APPLICATIONS

This application claims the benefit of and priority to U.S. Provisional Patent Application No. 61/990,295 filed on May 8, 2014, which is hereby incorporated by reference in its entirety.

FIELD OF THE INVENTION

The present invention relates to the field of implantable lumens, such as grafts to replace blood vessels.

BACKGROUND

Cardiovascular disease is the leading cause of death worldwide. Although drug treatment of cardiovascular disease is increasing, two of the primary methodologies currently used to treat cardiovascular disease are coronary artery bypass grafts and percutaneous coronary intervention, commonly referred to as angioplasty.

During an angioplasty procedure, a stent is often implanted into a restricted blood vessel to open the diameter of the blood vessel. Various types of stents are currently known for such procedures. Each type of stent has certain advantages, but each type also suffers from one of several known complications or weaknesses, including: restenosis, the need for long term use of anticoagulants, inhibition of natural blood vessel motion (such as pulsatile motion), in-stent thrombosis, improper healing, and potential for fracture of the stent.

In contrast to percutaneous coronary intervention, a coronary artery bypass graft implants a graft to bypass a blockage or obstruction in a coronary artery. Various types of grafts have been used for bypass surgeries, including biological grafts (e.g. autografts, allografts and xenografts) as well as artificial grafts (e.g. ePTFE, PTFE and PET). Additionally, although not widely used, tissue-engineered grafts are being developed in which the graft is produced in vitro.

Although each of the known grafts has certain advantages, such as cost, availability or similarity to native tissue, each of the known grafts also suffers from one of several known complications or weakness. For instance, autografts typically have shorter durability and higher incidences of failure rate compared with artificial grafts, while allografts typically require long term use of anti-rejection medication. Artificial grafts are readily available, but may be more prone to infection, thrombosis or intimal hyperplasia and may require long term use of medication, such as anticoagulants. Although tissue-engineered grafts overcome many of the problems associated with commonly-used biological and artificial grafts, tissue-engineered grafts are extremely expensive and take a long time to manufacture.

In general, native vessels remain the preferred choice for revascularization procedures, however, such tissues are not always available. In such cases, synthetic materials such as expanded polytetrafluoroethylene and polyethylene terephthalate have been used successfully as vascular conduits when the graft diameter exceeds 6 mm. Results have been poor, however, with grafts less than 6 mm in diameter, due to the development of thrombi and intimal hyperplasia.

These and other drawbacks are associated with current implantable lumens and methods used for forming implantable lumens.

BRIEF DESCRIPTION OF THE INVENTION

Exemplary embodiments are directed to a composite lumen and methods of forming a composite lumen, including degradable, endogenous grafts and braided grafts having a variable braid angle.

In one embodiment, a composite lumen includes a tubular textile formed of yarns having a first tensile strength and a matrix material in which the tubular textile is embedded to form a conduit having a bore and a sidewall substantially impermeable to liquid. The matrix material has a second tensile strength that is lower than the first tensile strength.

In another embodiment, a method for producing a composite lumen includes selecting yarns having a first tensile strength, selecting an elastomeric matrix material having a second tensile strength that is lower that the first tensile strength, forming a tubular textile of the yarns, and embedding the tubular textile in the matrix material to form a conduit having a bore and conduit walls that are substantially impermeable to liquid. The elastomeric matrix material is a biodegradable or bioresorbable polyester.

Other features and advantages of the present invention will be apparent from the following more detailed description, taken in conjunction with the accompanying drawings which illustrate, by way of example, the principles of the invention.

BRIEF DESCRIPTION OF THE DRAWINGS

Wherever possible, the same reference numbers will be used throughout the drawings to represent the same parts.

DETAILED DESCRIPTION OF THE INVENTION

Provided are a composite lumen and a method of forming a composite lumen. Embodiments of the present disclosure, for example, in comparison to concepts failing to include one or more of the features disclosed herein, facilitates pulsatile flow, provides gradient compliance, provides a biodegradable lumen, facilitates endogenous regeneration, increases biocompatibility, or a combination thereof.

Referring now to the figures in general, a composite lumen 10 includes a textile structure 20 and a matrix material 50. The textile structure 20 includes a reinforcing textile structure embedded with the matrix material 50. The matrix material 50 forms a wall 17 around the textile structure 20 that is substantially impermeable to liquid. In this way, the textile structure 20 and matrix material 50 combine to form a lumen 10 having liquid impermeable walls and a bore 15 through which fluid may flow.

The lumen 10 provides a hollow vessel able to withstand arterial pressure when it is implanted. In one embodiment, an interior and/or exterior of the composite lumen 10 may also include a coating material. For instance, the interior of the lumen 10 may be coated with Heparin to impede blood clotting within the vessel. In another embodiment, the lumen 10 is designed to biodegrade and/or bioresorb over time. After implantation, the lumen 10 provides a structure upon which the patient remodels vascular tissue. For instance, the lumen 10 may provide a structure upon which a neoartery is formed as the grafts biodegrades and/or bioresorbs. Additionally, although the graft is formed to enable rapid remodeling of tissue by the host, the lumen 10 may be cell-free, meaning that biological cells have not been seeded or formed into the lumen 10.

Figure 1:
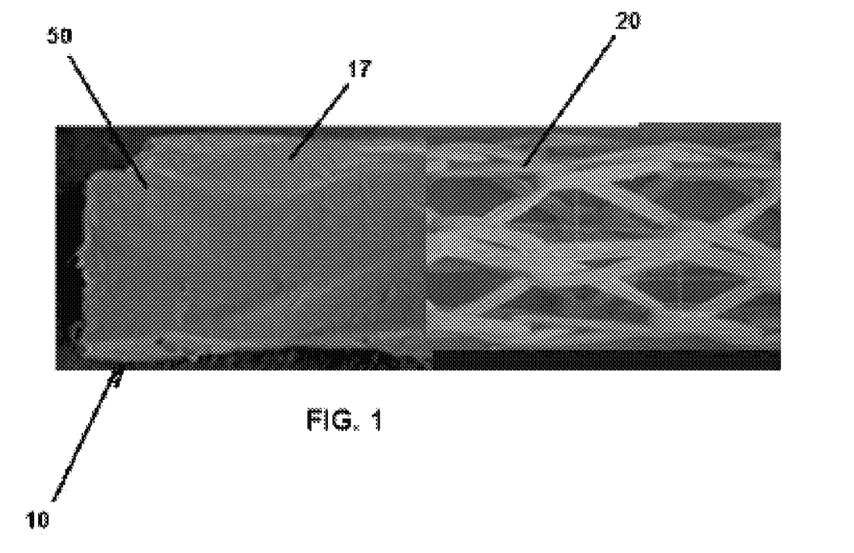
FIG. 1 is a side view of a portion of a composite lumen with reinforcing textile and resorbable matrix.
Figure 3:
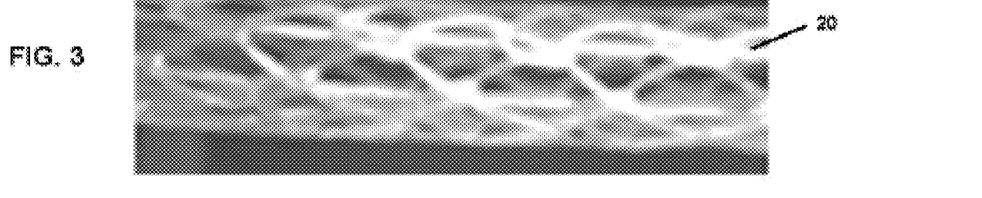
FIG. 3 is a side view of the reinforcing textile of the composite lumen illustrated in FIG. 1.
Figure 4:
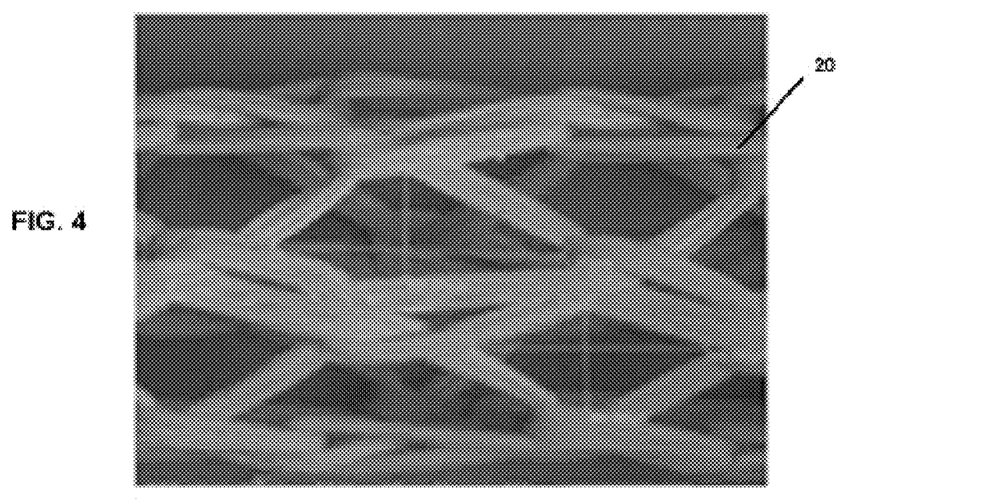
FIG. 4 is an enlarged fragmentary view of the reinforcing textile illustrated in FIG. 3.
Figure 5:
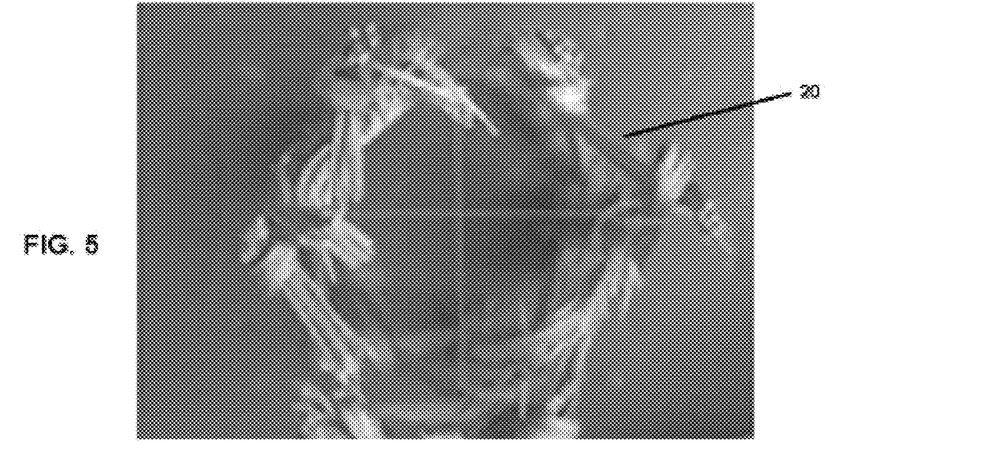
FIG. 5 is an enlarged end view of the reinforcing textile illustrated in FIG. 3.

In FIG. 1, a portion of the lumen 10 is illustrated with the matrix material 50 removed to show the underlying textile structure 20. In FIGS. 3-5, the textile 20 is illustrated before being embedded in the matrix material 50. The textile structure 20 is formed of any suitable material, and may be the same as, similar to, or different from the matrix material 50. For example, in one embodiment, the textile structure 20 is formed of a material having a higher modulus of elasticity and a higher tensile strength than the matrix material 50. In another embodiment, the matrix material 50 is a biodegradable and/or bioresorbable material. In a further embodiment, the textile structure 20 is also formed of a biodegradable and/or bioresorbable material. Alternatively, the matrix material 50 may include a biodegradable and/or bioresorbable material while the textile structure 20 is formed of a material that does not biodegrade or bioresorb. Materials that partially degrade may also be employed for the matrix 50 and/or textile structure 20 and which can be doped with a drug, so that the drug elutes from the article as the material degrades.

Referring to FIGS. 3-5, the textile structure 20 is an open structure including large openings formed between strands of the fibers thereof. For instance, the textile 20 may be formed as an open weave structure in which the warp yarns generally do not come together, thereby leaving interstitial openings in the structure. Such an open structure provides openings through the sides of the structure that are larger than the diameter of the yarns. More specifically, the openings may be more than twice the thickness of the yarns. Some of the openings may be more than five times the thickness of the yarns. Configured in this way, the textile structure 20 provides a framework or scaffold to be encased within the matrix material 50.

The textile scaffold 20 is formed of any of a variety of yarns. For instance, one or more monofilament or multifilament yarns may be used to knit the structure. The yarns may be formed of a variety of materials that may be biodegradable and/or bioresorbable, however, as discussed above, in some applications it may be desirable to use a yarn that is not biodegradable or bioresorbable. Exemplary yarns include yarns within the range of 5-200 denier formed of polymeric material, such as polylactic acid thermoplastic (PLA), polyglycolide (PGA), poly L lactic acid (PLLA), poly(lactic-co-glycolic acid) (PLGA), poly(glycerol sebacate) (PGS), poly(glycerol sebacate) urethane (PGSU), polycaprolactone (PCL), 2-pyran-2-one-4,6-dicarboxylic acid (PDC), poly-p-dioxanone (PDO), polydioxanone (PDS), poly(1,8-octanediol citrate) (POC) and collagen.

Another alternate methodology for embedding is coating the yarn used for the textile structure 20 with the matrix material 50 prior to weaving, knitting or braiding. For instance, textile yarn may coated in the matrix material 50 via dip bath, or spraying. If coating is employed, pressure tooling and specialized heated chambers may be used to cure the yarn such that the matrix material 50 adheres to the fibers. This allows a greater adhesion between the matrix material and the textile fiber prior to final formation by increase the wetting of the polymer to the yarn and managing the mechanical energy at the interlaces and fibril bundles. It also enhances local elastomeric intimacy between the matrix material 50 and the yarn filaments, creating a unified "bundle" of coated fibers that help to manage energy such as from pulsatile action. These coated yarns can then be used in the braid construction as a composite filament.

The textile scaffold 20 forms a support structure having sufficient radial strength to impede kinking or pinching that would reduce the internal opening of the composite lumen 10. Additionally, the textile scaffold 20 is formed to allow sufficient axial elongation so that the lumen is able to stretch and contract axially, while increased radial force aids in keeping the lumen 10 open when bent.

Any one of a number of methods may be used to form the textile scaffold 20, including, but not limited to knitting, weaving, and/or braiding. For example, in one embodiment, the textile scaffold 20 includes a knit structure. Suitable knit structures include, but are not limited to, a warp knit, a circular warp knit fabric, a circular weft knit fabric, or a combination thereof. In another embodiment, the knit or other structure of the textile scaffold 20 facilitates expansion and contraction of the textile scaffold 20. In a further embodiment, the expansion provided by the structure of the textile scaffold 20 is greater than the expansions and/or extension provided by the elasticity of the yarns themselves.

In one embodiment, the textile scaffold 20 includes a braided structure. A pitch within the braided structure is adjusted and/or controlled to vary compliance (both radial expandability and compressibility) within the composite lumen 10, which may be different at different regions along its length, with a change in pitch being used to provide control over radial expandability. For example, an increased pitch decreases a compliance of the lumen 10 and/or forms the lumen 10 including a more limited diameter as compared to a braided structure including a lower decreased pitch, although both could be still be part of the same, continuously braided structure. In another embodiment, the textile scaffold 20 includes multiple layers that at least partially adjust compliance, porosity, permeability, or a combination thereof.

Figure 2:
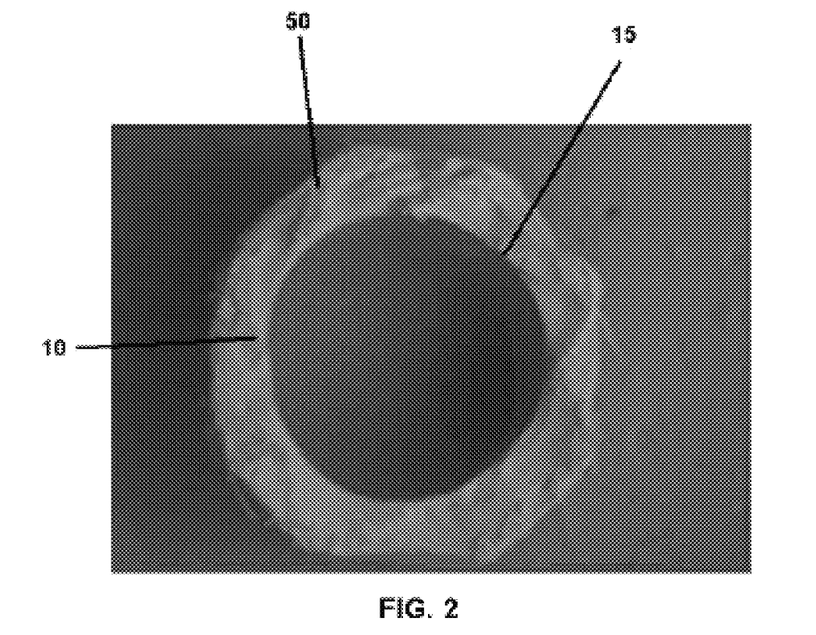
FIG. 2 is a left end view of the composite lumen illustrated in FIG. 1.

Referring to FIGS. 1-2, the matrix material 50 is a flexible material, such an elastomeric material that provides axial and/or radial stretching of the lumen 10. Suitable elastomers include, but are not limited to, biodegradable elastomers, elastomers formed of biocompatible monomers, cross-linked esters, cross-linked polyester elastomers, poly(glycerol sebacate), polyurethanes, polyurethane ureas, or a combination thereof. In one embodiment, the matrix material 50 is more elastic than the textile scaffold 20 and/or the individual yarns forming the textile scaffold 20. The textile scaffold 20 decreases and/or limits expansion of the matrix material 50, while the matrix material 50 decreases or eliminates a permeability of the textile scaffold 20. Together, the textile scaffold 20 and the matrix material 50 form the lumen 10 having variable compliance, increased suture retention, and/or decreased permeability.

In one embodiment, the matrix material 50 is selected to promote endogenous regeneration. In other words, the matrix material 50 may be selected so that it stimulates regenerative vessel and cell growth by recruiting or sustaining growth of endothelial cells. Through the recruiting and/or sustaining of cell growth, the matrix material is replaced by native or seeded tissue to regenerate the damaged vessel.

In some embodiments, the matrix material 50 is degraded by hydrolysis. The matrix material 50 may also biodegrade and/or is bioresorbed primarily through surface erosion, rather than bulk erosion. In other words, the primary erosion of the matrix material is directly proportional to the surface area of the material. Accordingly, since the lumen is relatively thin, the erosion of the matrix material is characterized by zero order since the rate of degradation is generally or substantially constant. The result is that the lumen 10 thins over time while maintaining its bulk integrity.

The use of variable angle braiding in single and double layer structures permits selective control of the compliance and/or density of the scaffold 20 along its length. The scaffold 20 may be embedded by the bioresorbable matrix material 50 to result in a combination of a dynamic textile system and an elastic biopolymer that can provide similar compliance at anastomosis, enabling a seamless connection of synthetic and biologic materials with comparable elasticity. The use of the bioresorbable material means that exemplary embodiments can further stimulate regenerative vessel healing and cell growth, while preventing occlusion and eventually degrading to leave only the native tissue behind, essentially creating a new artery or other vessel.

Thus, the combination of the compliance of the braiding with the compliance of the bioelastomer creates a pulsatile blood tight vessel. Further, varying the braid angle can provide gradient compliance so that the there is more pulsatile response at the distal end of the graft than at the proximal end. The ability to vary braid angle at distal and proximal ends of a graft also gives control over managing hemodynamic flow and can reduce turbulence at the point the graft is attached to the blood vessel.

The combination of two compliant structures to create a composite synthetic vessel provides numerous other benefits including high suture retention and constrained elasticity as a result of the textile reinforcement of the braiding while also lowering permeability and stimulating regenerative vessel healing through the bioelastomer matrix. Exemplary embodiments thus create an engineered synthetic vessel having controlled, selective, variable compliance, which may be tailored to specific desired performance characteristics based on specific anatomies (e.g. compliance of vein versus arterial tissue).

Figure 14:
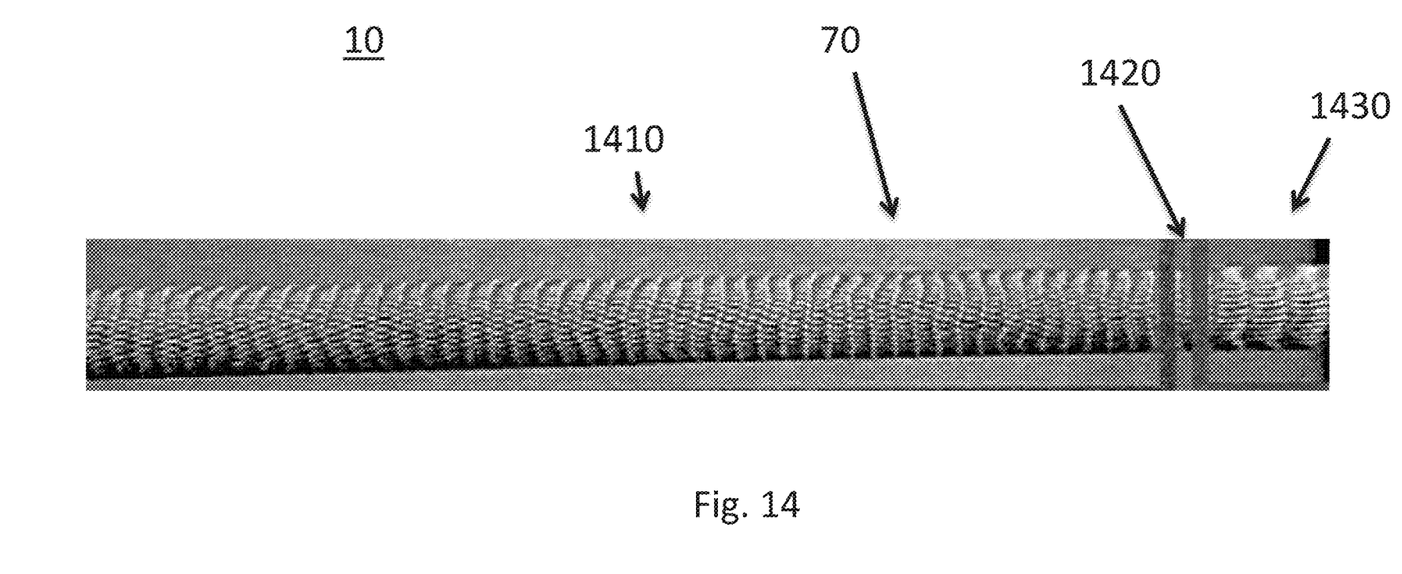
FIG. 14 illustrates a braided article having different braid angles at different locations along its length.

The variation in braid angle may depend on a variety of factors pertaining to the end use of the lumen or other article being formed, as well as anatomical characteristics of the patient or class of patient into which the article will be implanted. Thus, some embodiments may have, for example, a high braid angle to achieve a high density region along one length of the lumen 10 while another portion of the same lumen 10 will have a low braid angle to achieve a low density region, all while being part of a single, continuous braided structure. FIG. 14 illustrates a metallic scaffold 70 of a lumen 10 having a low density, high braid angle region 1410 and a high density, low braid angle region 1430 at a different portion along its length with a transition region 1420 in which the braid angle transitions from one braid angle to another.

It will be appreciated that the number and location of different density regions (and thus the number of variations in the braid angle), as well as the specific density of any particular region along the length of the lumen 10 may change depending on application and that variation from one braid angle to another may occur over gradually over a transition region and the braid angle may change any number of times as desired within a particular lumen. A wide range of braid angles may be employed, such as from 30 degrees up to 170 degrees, corresponding generally from about 10 to about 200 picks per inch, providing an ability to vary the braid angle across a wide range. For low density regions, the braid angle is typically from about 30 degrees to about 130 degrees, while for high density regions, the braid angle may be in the range of about 130 degrees to about 170 degrees.

Among the advantages of embodiments that employ a braided composite construct for the lumen 10, are that conventional technologies which depend on electrospin or tubular-only structures often fail from lack of burst strength from premature "scaffold crashing" in which the non-reinforced material prematurely degrades and loses its ability to support pulsatile physiological pressures as tissue mass increases. Exemplary embodiments are not susceptible or much less likely to be susceptible to such failures.

In addition or alternative to braiding, it will be appreciated that non-interlaced bidirectional fiber wrapping could be used. In still other embodiments, the matrix material may be extruded first, followed by braiding over that core. This may have some advantages in providing a smooth inner diameter. The outer braiding may be infiltrated with another polymer material which may be the same or different as that used in forming the core. Accordingly, yet another advantage is the ability to vary the inner wall thickness from the outer wall thickness where the endothelialized surface degrades in a differential manner from the outer wall where the muscle layer colonizes.

Additionally or alternatively, as illustrated in FIGS. 6-13, the lumen 10 includes a metallic structure 70 having a combination of different diameter wire strands. For example, the metallic structure 70 may include a braided metallic structure having multiple fine diameter wire strands 71. The multiple fine diameter wire strands 71 include any suitable number of wire strands, and may be varied to provide desired properties of the lumen 10. In one embodiment, the metallic structure 70 includes at least one increased diameter wire 73, the increased diameter wire 73 having an increased diameter as compared to the fine diameter wire strands 71. In another embodiment, the increased diameter wire 73 forms a helix extending in the same spiral direction as the fine diameter wire strands 71. In a further embodiment, the metallic structure 70 includes at least two of the increased diameter wires 73 helically extending in the same spiral direction as the fine diameter wire strands 71. The one or more increased diameter wires 73 form resilient coil portions, such as, but not limited to, spring-like structures within the metallic structure 70.

The metallic structure 70 includes any suitable braid style, wire amount, and/or wire size. Although disclosed with respect to metallic wire strands, it will be appreciated that the embodiments described with respect to FIGS. 6-13 are not so limited and that other filament material may be used instead of, or in combination with the metallic wire strands. One suitable braid style includes, but is not limited to, a maypole style braid. Suitable wire amounts include, but are not limited to, at least 10 wire ends, at least 12 wire ends, at least 20 wire ends, at least 30 wire ends, 24 wire ends, 36 wire ends or more, or any combination, sub-combination, range, or sub-range thereof. Suitable wire sizes include, but are not limited to, at least 0.0005 inches, at least 0.001 inches, between about 0.001 and about 0.01 inches, between about 0.001 and about 0.005 inches, about 0.001 inches, about 0.002 inches, about 0.003 inches, about 0.004 inches, about 0.005 inches, or any combination, sub-combination, range, or sub-range thereof.

Figure 6:
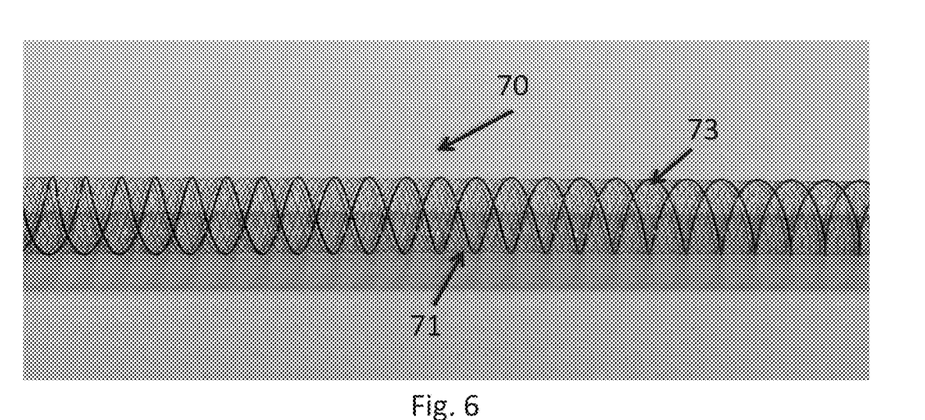
FIG. 6 is a perspective view of a metallic structure according to an embodiment of the disclosure.
Figure 7:
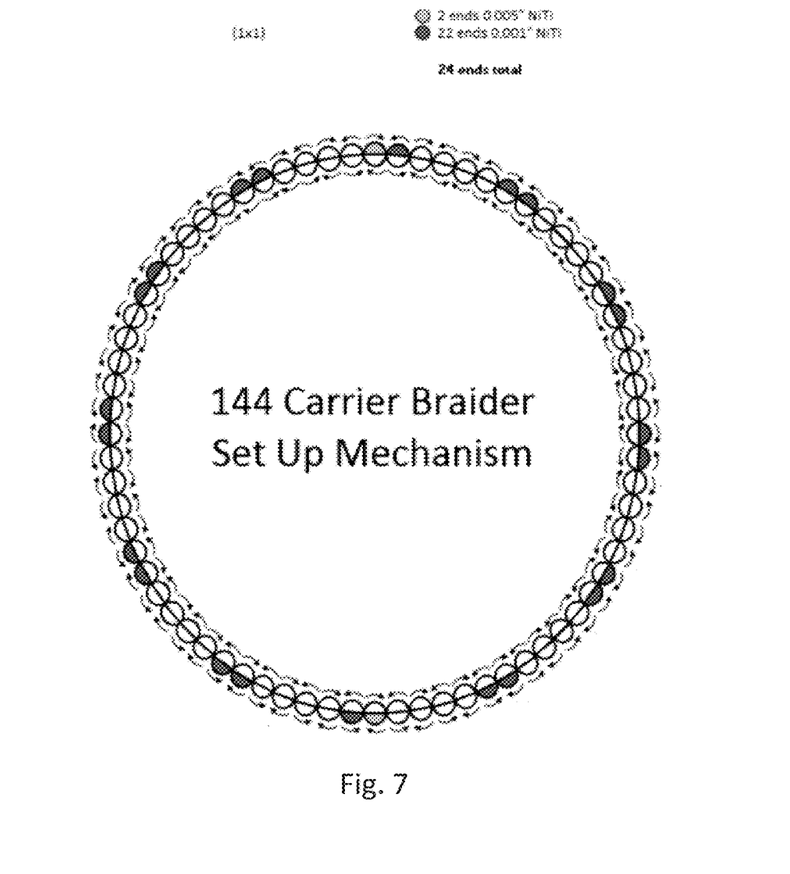
FIG. 7 is a schematic view of a carrier setup for forming the metallic structure of FIG. 6.

For example, as illustrated in FIGS. 6-7, the metallic structure 70 includes a maypole style braid including 24 total ends of wire. The 24 total ends of wire including 22 ends of 0.001 inch Nitinol and 2 ends of 0.005 inch Nitinol. The 0.005 inch Nitinol forms the increased diameter wire 73, and is evenly spaced in every $12^{th}$ end spiraling around the metallic structure 70 in a clockwise direction with a braid angle of about 110°.

Figure 8:
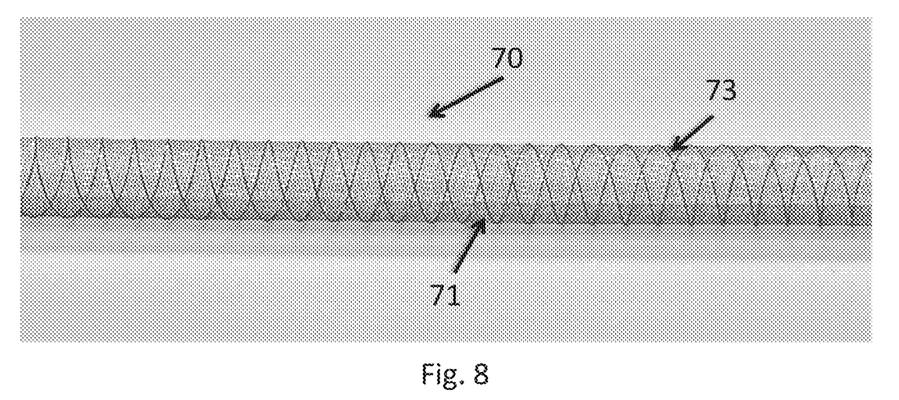
FIG. 8 is a perspective view of a metallic structure according to an embodiment of the disclosure.
Figure 9:
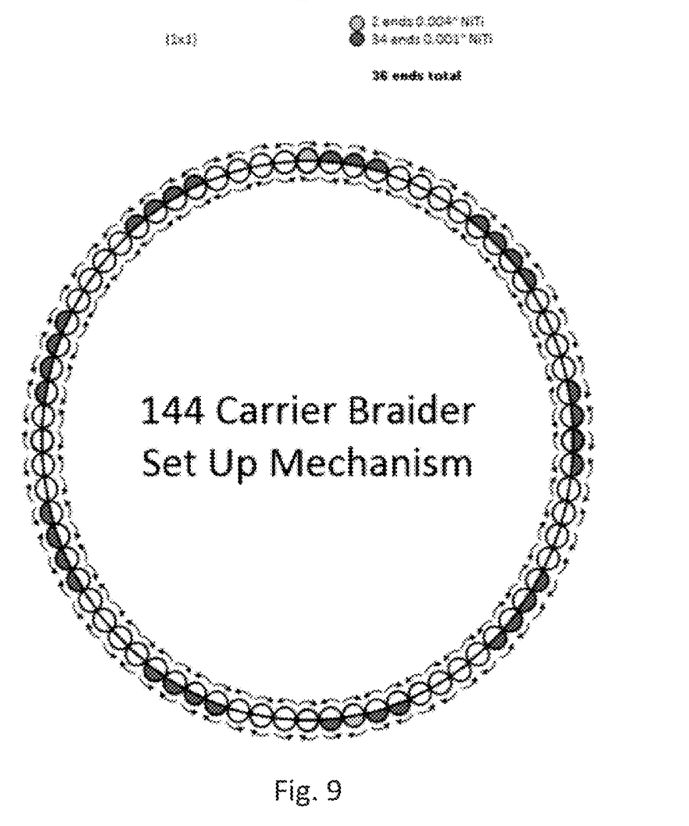
FIG. 9 is a schematic view of a carrier setup for forming the metallic structure of FIG. 8.

In another example, as illustrated in FIGS. 8-9, the metallic structure 70 includes a maypole style braid including 36 total ends of wire. The 36 total ends of wire including 34 ends of 0.001 inch Nitinol and 2 ends of 0.004 inch Nitinol. The 0.004 inch Nitinol forms the increased diameter wire 73, and is placed in carriers 1A and 35A, end spiraling around the metallic structure 70 in a clockwise direction with a braid angle of about 110°.

Figure 10:
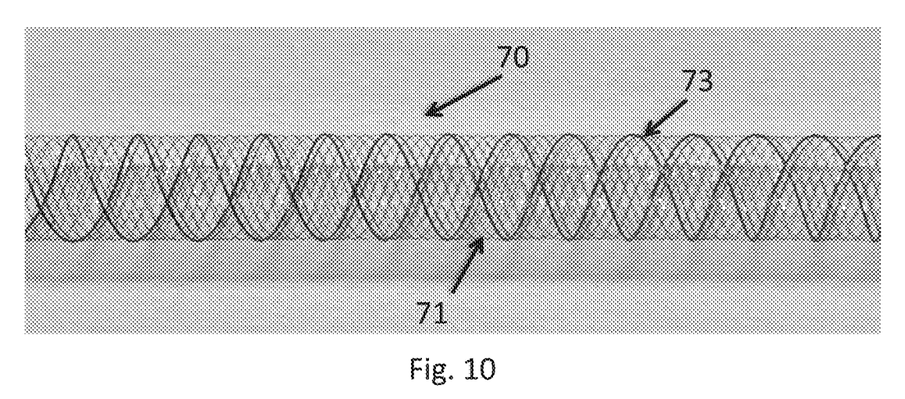
FIG. 10 is a perspective view of a metallic structure according to an embodiment of the disclosure.
Figure 11:
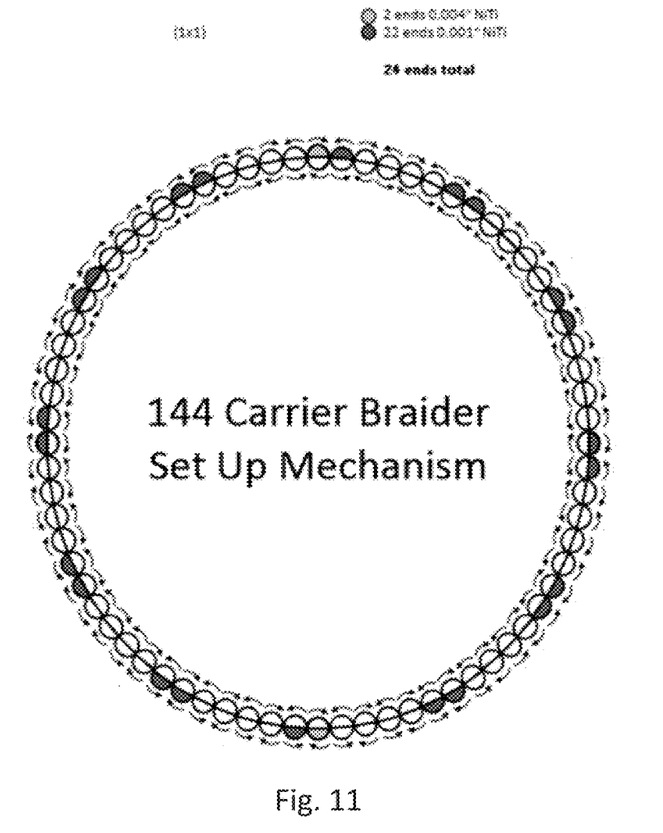
FIG. 11 is a schematic view of a carrier setup for forming the metallic structure of FIG. 10.

In another example, as illustrated in FIGS. 10-11, the metallic structure 70 includes a maypole style braid including 24 total ends of wire. The 24 total ends of wire including 22 ends of 0.001 inch Nitinol and 2 ends of 0.004 inch Nitinol. The 0.004 inch Nitinol forms the increased diameter wire 73, and is evenly spaced in every $12^{th}$ end spiraling around the metallic structure 70 in a clockwise direction with a braid angle of about 110°.

Figure 12:
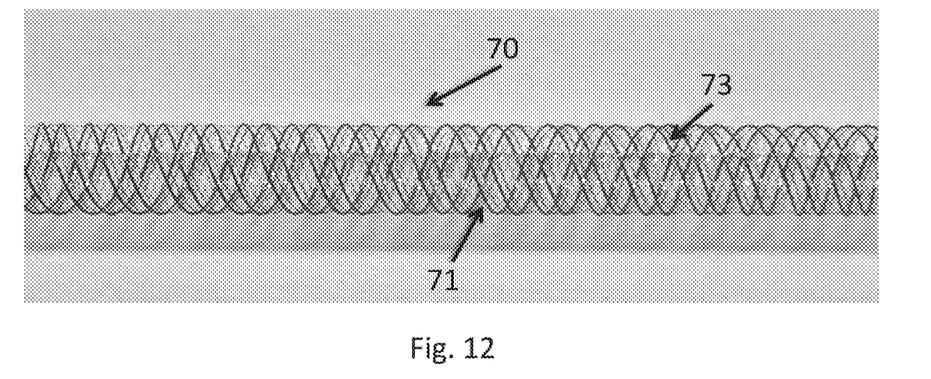
FIG. 12 is a perspective view of a metallic structure according to an embodiment of the disclosure.
Figure 13:
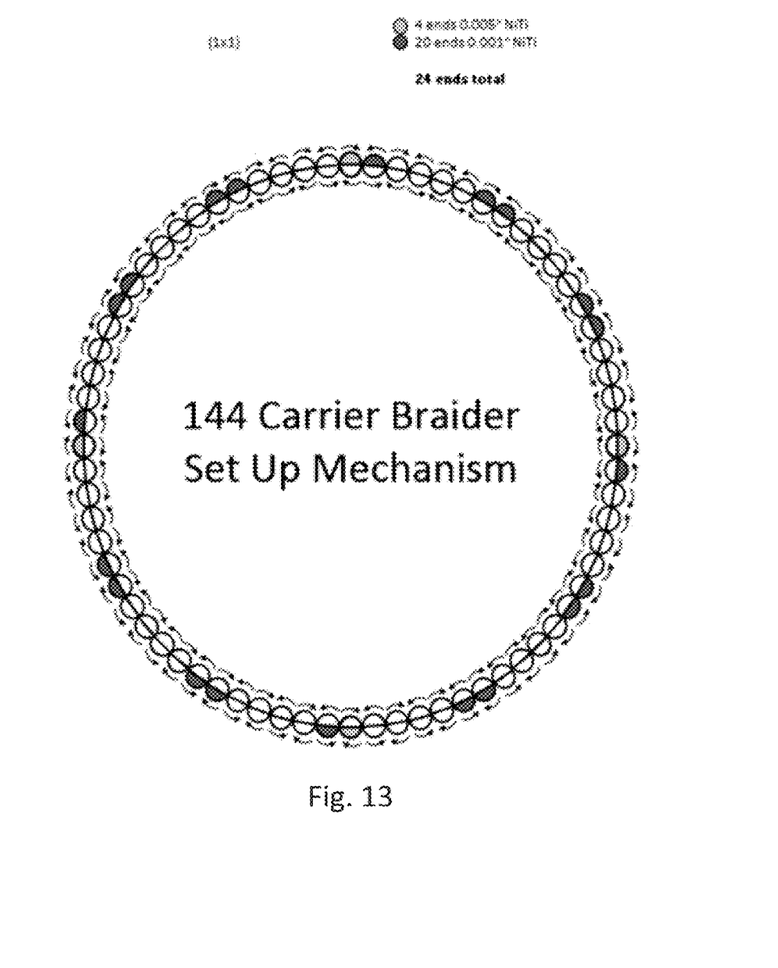
FIG. 13 is a schematic view of a carrier setup for forming the metallic structure of FIG. 12.

In another example, as illustrated in FIGS. 12-13, the metallic structure 70 includes a maypole style braid including 24 total ends of wire. The 24 total ends of wire including 20 ends of 0.001 inch Nitinol and 4 ends of 0.005 inch Nitinol. The 0.005 inch Nitinol forms the increased diameter wire 73, and is evenly spaced in every $6^{th}$ end spiraling around the metallic structure 70 in a clockwise direction with a braid angle of about 110°.

The helical orientation of the increased diameter wires 73, as compared to crossed wires and/or the fine diameter wire strands 71 alone, increase radial compression resistance, provide a lower profile, facilitate compressibility while maintaining an increased radial strength, increase recovery, increase structure stability of the metallic structure 70, uses less material, or a combination thereof. Additionally, the helical orientation of the increased diameter wires 73 facilitate compression and extension in a longitudinal direction, which is not possible with crossed wires. In one embodiment, the metallic structure 70 forms the lumen 10 without the matrix material 50. For example, the metallic structure 70 without the matrix material 50 may be used for clot retrieval, as a base structure of a hose, to add stability to other tubular structures, in peripheral artery disease treatment, in neurovascular aneurysm treatment, in various stent applications, or a combination thereof.

Method of Production

In one embodiment, the tubular mesh structure is formed of interlaced yarns. The tubular structure 50 may be formed by circular warp knitting one or more yarns. For instance, in the present instance, eight multifilament yarns are knit together to form an open mesh tubular textile. The ends are distributed around the circumference of the circumference of the tubular structure and the yarns are knitted together. In the present instance, the knit pattern includes a crossover pattern, such as a 1-4 outside crossover pattern.

The tubular textile may be formed in a variety of diameters so that the interior diameter of the structure ranges from about 1 mm to about 6 mm. However, in certain application it may be desirable to form the structure so that the interior diameter is between about 6 mm and about 10 mm. In still further applications, it may be desirable to form the structure so that the interior diameter is greater than 10 mm.

In one or more of the embodiments disclosed herein the tubular structure is heat set after it is formed. For instance, the knit structure may be mounted onto a mandrel and then exposed to elevated temperature, meaning that the knit structure is exposed to a temperature above the ambient room temperature at which the structure is knit. However, it should be understood that if the textile is heat set, the temperature and the duration of the step of heat setting may vary based on the composition of the yarn and the formation of the textile structure. The process of heat setting provides dimensional stability so that the structure is more likely to rebound or return to its original form when bent or stretched.

Once formed, the tubular textile 20 is embedded into a biodegradable or bioresorbable matrix material 50. If the textile is heat set on a mandrel, the textile may remain on the mandrel when embedding the textile into the matrix material. However, in the present instance, the textile is removed from the heat setting mandrel prior to embedding it in the matrix material.

The matrix material forms a continuous or substantially continuous wall that is liquid impermeable or substantially liquid impermeable so that fluid, such as blood does not leak through the wall of the lumen. The thickness of the matrix material may vary based on the application. However, preferably the matrix is sufficiently thick to retain integrity when the interior bore is exposed to fluid under pressure. Specifically, the matrix material provides sufficient radial strength to maintain wall integrity when exposed to arterial pulse pressure.

The textile may be embedded into the matrix material in one of several ways. For instance, the textile may be dipped into a bath of matrix material. After the textile is dipped into the matrix material, the matrix material adheres to the textile to form a coating on the textile. The coated structure is then dried or cured. The coated structure may be hung in an ambient atmosphere to dry, however, in the present instance, the coated structure is placed in an airtight chamber to which a desired level of vacuum is then applied and the temperature of the chamber is elevated above ambient temperature to dry the coating of matrix material. For instance, in the present instance, after dipping, the structure may be placed into a vacuum oven and dried at over 100° C. The dipping and drying processes may be an iterative process to gradually build up the thickness of the matrix material on the textile structure. For instance, the textile may be dipped into the bath of matrix material five to ten times with a step of drying between each coating.

An alternate methodology for embedding the textile is to extrude the textile and the matrix material. For instance, textile may be coextruded with the matrix material. Alternatively, the textile and matrix may use overjacketing extrusion. If overjacketing extrusion is employed, pressure tooling is utilized so that the melted matrix material contacts the textile well before reaching the extrusion die to promote adhesion between the matrix material and the textile. Other alternative methods for coating the textile with matrix material include liquid molding, cast sheet wrap, spraying, and shrink wrapping.

A porogen may also be incorporated into the matrix material to control the porosity of the matrix material. The size and amount of porogen is selected to provide the desired amount of porosity. After the matrix material is cured, the structure is immersed in a bath of an appropriate solvent to dissolve the porogen material. If necessary the structure is then rinsed to wash away the porogen solvent. Depending on the method for embedding the matrix material, the process of dissolving the porogen may be performed iteratively as layers of matrix material are applied to the textile structure.

Additionally, after forming the lumen, the lumen may be subjected to a sterilization process. For instance, the lumen may be subjected to radiation sterilization, such as ε-beam, γ-irradiation or other radiation. Alternatively, other forms of sterilization may be used, such as gas sterilization using ethylene oxide, dry heat or autoclave.

Configured as described above, the composite lumen 10 may be used in a variety of applications, such as a cardiovascular graft to repair or replace a damaged blood vessel. The lumen structure may be a small bore vessel having an interior diameter of less than 6 mm, but still resist kinking when bent. Additionally, the composite lumen resists axial compression but allows pulsatile expansion. Further, when stretched axially, the composite lumen resists deforming radially, which would narrow or occlude the bore of the lumen. In this way, the composite lumen provides a graft having tissue compliance similar to the patient's native vascular tissue. For instance, the lumen can taper in an axial orientation similar to arterial or venous anatomy.

The composite lumen also has improved suture retention. Specifically, the embedded textile structure provides a structure having greater tensile strength than that of the matrix material. As such, the textile structure limits displacement of sutures axially along the length of the lumen, thereby impeding the likelihood of the sutures ripping through the wall of the lumen.

Furthermore, the composite lumen provides a biodegradable or bioresorbable framework that promotes regeneration of the damaged vessel. Alone, the textile structure of the composite lumen provides little to no support of tissue regeneration. The matrix material provides the cellular foundation to initiating the regenerative process. For example, when the matrix material is composed of a PGS based polymer, tissue regeneration can proceed due to the composite lumen creating a low inflammatory, bio-inert environment for tissue healing. As the vessel regenerates, the composite lumen biodegrades and/or resorbs so that eventually the lumen is replaced by native tissue.

Additionally, the matrix material provides a non-adhesive surface to protect the injury site from tissue adhesions and scar tissue formation. Fibrous in-growth to the injury site results in a disruption of the healing process resulting in scar formation opposed to tissue regeneration. Particularly when PGS is used as the matrix material, poor cell adhesion to the walls of the lumen avoids a common source of failure in conventional small bore lumens in which colonizing cells entering into lumen such as the endothelial cells, tend to adhere to the side walls. This hang-up promotes cell death and subsequent inflammation, thereby promoting the immune system response to clean up the cause of the inflammation. Conversely, poor cell adhesion in the use of PGS as the matrix material may give rise to properties of bio inertness, non-inflammatory and pro-cell growth.

According to certain embodiments disclosed herein, one method of forming the metallic structure 70 includes braiding the metallic structure 70 on a 144 carrier maypole style braider with a puller system, a 48 carrier maypole style braider with a puller system, or a 24 carrier maypole style braider with a puller system. The carriers are loaded according to any desired configuration, such as, but not limited to, and one of the embodiments disclosed herein. The wires are braided onto any suitable mandrel, such as a stainless steel 4 millimeter diameter mandrel. The distance from puller to braid point is set to achieve a desired braid angle, such as, but not limited to, a 110° braid angle. A speed of the braider is set to any suitable braiding speed. One suitable braiding speed includes, but is not limited to, 90 rpm. Next, the wires, which are attached to the mandrel using stainless steel wire, are braided using the braider and puller system described above. After braiding, the mandrels may be heat-set at any suitable temperature for any suitable duration of time. In one embodiment, the mandrels are heat set at 520° C. for 10 minutes and quenched in water, and allowed to dry in ambient air. Post drying the braid is removed from the mandrel by cutting the stainless steel wires and manually removing the braid from the mandrel.

EXAMPLES

The exemplary embodiments are further described with respect to the following example, which are presented by way of illustration and not of limitation.

Example 1

A 1/56/28/0z PGA multifilament yarn was used to produce a textile scaffold as shown in FIG. 1. The yarn had a denier of 56+/−3, a tenacity >5.5 grams per denier and elongation of 30+15%/−8%.

Eight yarns were knit over a 2 mm mandrel. Each yarn equates to a wale and the wales were distributed around the circumference. The yarns were knit using a circular warp knit pattern with a 1-4 outside crossover pattern similar to a 1-0, 4-5 stitch pattern to form a tubular structure having approximately 54 courses per inch and the wales were 20-22 courses per inch. After knitting, the fabric was scoured to remove the spin finish. The knit structure was then heat set in an inert atmosphere oven.

After heat setting, the textile was removed from the mandrel and embedded into the matrix material using a dip coating technique. The matrix material was a bath of 30% poly(glycerol sebacate) (PGS)/70% 1,3-dioxolane. The tubular structure was immersed into the matrix material for one minute then hung for 15 minutes. The structure was then placed in a vacuum oven at 120° C. for two hours. The dipping and curing process described above was repeated twice during the first day for a total of three coats the first day. The process was repeated each of the next two days for a total of three days of coating with three coats applied per day.

Example 2

In a second example, a double layer braided structure was formed using a multifilament PGA fiber that was coated with PGS.

The first layer composed of 72 ends of 1/56/28/0 PGA multifilament yarn was braided in a 2×2 configuration at 120 picks per inch (PPI) on a 4 mm mandrel. A second layer composed of 48 ends of 1/56/28/0 PGA multifilament yarn was then braided over the first layer in a diamond pattern at 50 PPI. The double layer braid was then heat treated at 180° C. for 10 minutes to stabilize the structure before removing it from the 4 mm mandrel.

Once the heat treatment is complete the double layer braid was removed from the mandrel and soaked in 70% (wt) isopropyl alcohol for 30 minutes. After soaking, the braid was dip coated twice in 20% (wt) PGS solution in ethyl acetate and cured for 48 hours in a vacuum oven at 120° C. and about 8 Torr to produce a resultant structure that was a compliant water tight vessel.

By modifying the picks per inch along the length of the braid structure, the pitch of the fibers is controlled and, as a result, the expansive properties of the braid (i.e., compliance).

Additional examples were created using PGA and PCL while varying the PPI of the braid structures at different levels, including 35 to 15 PPI and 25 to 10 PPI.

It will be recognized by those skilled in the art that changes or modifications may be made to the above-described embodiments without departing from the broad inventive concepts of the invention. For instance, in the foregoing description, the textile is described as being formed using eight yarns. However, the textile may be formed using a different number of yarns, such as 12 ends, 16 ends or more. Additionally, the hollow lumen has been described as a structure for repairing damaged cardiovascular blood vessels. However, the composite lumen can also be used in a variety of other applications, such as a structure enabling arterio venous access in patients, such as patients with renal disease. Still further applications include, but are not limited to repairing or replacing pharynx, larynx, renal, ureter, urethra, intestine, ducts, bronchi, fallopian tube, uterus, trachea, oral and anal structures, as well as other tubular mammalian structures. Accordingly, it should be understood that the lumen can be utilized in vivo in applications that are not directed to fluid flow (such as a blood vessel). For instance, the lumen can be utilized in various entubulation applications, such as a nerve guidance conduit or a nerve cuff in which during reconstructive surgery, nerve endings are inserted into opposing ends of the composite lumen. The lumen can also be utilized in void filler applications, such as a brain aneurysm blockage, a nucleus pulposus replacement and an annulus fibrous ring. In addition to in vivo applications, the composite lumen may be incorporated into other structures to provide kinkless hoses, PEX tubing, reinforcement, IV lines, inner tubes and other flexible tubular constructs.

Still further, the yarns used to create the textile scaffold may be modified to incorporate a bioreactive component in a delivery structure designed to provide a controller release of the bioactive component. Additionally, although the textile has been described as a single layer structure, it should be understood that the textile may be formed of multiple concentric layers.

Example 3

To illustrate the ability of the matrix material to create a cell-friendly, pro-healing environment, PGS was tested with respect to Schwann cell cytocompatibility, protein absorption, and Schwann cell attachment. Cytocompatibility conducted using extracts (7 d, 14 d, 21 d, and 28 d) of 24 and 48 hour cured PGS showed little to no change when compared to tissue culture polystyrene indicating excellent cell compatibility. Cured PGS films also demonstrated absorption of laminin and fibronectin which are proteins present in the extra-cellular matrix and play an important role in tissue regeneration.

Cell adhesion experiments performed with human and rat Schwann cells on 24 h, 48 h and 96 h cured PGS films showed less than 25% adhesion. These results suggest a low occurrence of potential extraneous tissue attachments, e.g., fibroblasts. Furthermore, there is greater potential for Schwann cells to migrate to the distal stump opposed to growing into the composite lumen resulting in a higher occurrence of nerve regeneration.

It should therefore be understood that while the invention has been described with reference to one or more embodiments, various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In addition, all numerical values identified in the detailed description shall be interpreted as though the precise and approximate values are both expressly identified.

What is claimed is:

1. A composite lumen, comprising:
   a tubular textile formed of yarns having a first tensile strength, the tubular textile including interstitial openings therein; and
   an elastomeric matrix material in which the tubular textile is embedded, the matrix material infiltrating the tubular textile to form a radially distentive vascular graft including a conduit having a bore with a diameter in the range of about 1 mm to about 6 mm and a sidewall substantially impermeable to liquid and configured to withstand physiological arterial pressure;
   wherein the matrix material is a biodegradable or bioresorbable material having a second tensile strength that is lower than the first tensile strength,
   wherein matrix material of the vascular graft promotes endogenous growth of mammalian neovascular tissue; and
   wherein the matrix material comprises poly(glycerol sebacate).

2. The composite lumen of claim 1, wherein the tubular textile is woven, knit or braided.

3. The composite lumen of claim 2, wherein the tubular textile is a circular warp knit structure.

4. The composite lumen of claim 1, wherein the tubular textile is formed of biodegradable or bioresorbable material.

5. The composite lumen of claim 4, wherein the tubular textile comprises at least one composition selected from the group consisting of polylactic acid thermoplastic, polyglycolide, poly-L-lactic acid, poly(lactic-co-glycolic acid), poly(glycerol sebacate), polycaprolactone, 2-pyran-2-one-4,6-dicarboxylic acid, poly-p-dioxanone, polydioxanone, poly(1,8-octanediol citrate), and collagen.

6. The composite lumen of claim 1, wherein the composite lumen facilitates pulsatile flow.

7. The composite lumen of claim 1, wherein the tubular textile is configured to resist occlusion of the bore when an axial load is applied to the lumen.

8. The composite lumen of claim 1, wherein the tubular textile is a braided textile.

9. The composite lumen of claim 8, wherein the braided textile has a first braid angle along a first portion of its length and a second braid angle along a second portion of its length that is different from the first braid angle.

10. The composite lumen of claim 8, wherein the braided textile comprises metal wires of at least two different diameters in the braid.

11. The composite lumen of claim 10, wherein the metal wires having different diameters are spiraled in the same direction in the braid.

12. The composite lumen of claim 8, wherein the braided textile comprises poly(glycerol sebacate).

13. The composite lumen of claim 1 wherein the vascular graft is cell-free.

14. The composite lumen of claim 1, wherein the tubular textile consists of multi-filament biodegradable or bioresorbable yarns.

15. The composite lumen of claim 1, wherein the tubular textile is braided at 10-120 picks per inch.

16. The composite lumen of claim 1, wherein the tubular textile is braided with a braid angle between about 30 degrees to about 130 degrees.

17. A composite lumen, comprising:
a vascular graft having a bore, the bore having a diameter in the range of about 1 mm to about 6 mm, wherein the graft comprises:
a braided tubular textile comprising polyglycolide yarns; and
an elastomeric matrix comprising poly(glycerol sebacate) surrounding the braided tubular textile,
wherein the graft has a radially distentive sidewall substantially impermeable to liquid and is configured to withstand physiological arterial pressure, the elastomeric matrix having a tensile strength lower than a tensile strength of the polyglycolide,
wherein the elastomeric matrix promotes endogenous growth of mammalian neoartery tissue.

18. The composite lumen of claim 17 wherein the polyglycolide yarns are multi-filament yarns.

19. A composite lumen, comprising:
a braided tubular textile formed of multi-filament yarns having a first tensile strength,
the braided tubular textile infiltrated with a matrix material comprising poly(glycerol sebacate) to form a synthetic composite graft structure, the synthetic composite graft structure including a conduit having a bore with a diameter in the range of about 1 mm to about 6 mm and a sidewall substantially impermeable to liquid and configured to withstand physiological arterial pressure;
wherein the matrix material has a second tensile strength that is lower than the first tensile strength,
wherein matrix material of the vascular graft promotes endogenous growth of mammalian neovascular tissue.

* * * * *